(12) United States Patent
Sandanger

(10) Patent No.: US 10,602,255 B2
(45) Date of Patent: Mar. 24, 2020

(54) SUB TRAGIC EAR UNIT

(71) Applicant: FREEBIT AS, Oslo (NO)

(72) Inventor: Vidar Sandanger, Oslo (NO)

(73) Assignee: FREEBIT AS, Oslo (NO)

( * ) Notice: Subject to any disclaimer, the term of this patent is extended or adjusted under 35 U.S.C. 154(b) by 0 days.

(21) Appl. No.: 14/417,284

(22) PCT Filed: Jul. 29, 2013

(86) PCT No.: PCT/NO2013/050126
§ 371 (c)(1),
(2) Date: Jan. 26, 2015

(87) PCT Pub. No.: WO2014/017922
PCT Pub. Date: Jan. 30, 2014

(65) Prior Publication Data
US 2015/0215693 A1    Jul. 30, 2015

(30) Foreign Application Priority Data

Jul. 27, 2012    (EP) .................................... 12178314

(51) Int. Cl.
*H04R 1/10*    (2006.01)
*A61F 11/08*    (2006.01)

(52) U.S. Cl.
CPC ............... *H04R 1/10* (2013.01); *A61F 11/08* (2013.01); *H04R 1/105* (2013.01); *H04R 1/1016* (2013.01); *H04R 1/1083* (2013.01); *H04R 2201/107* (2013.01); *H04R 2460/09* (2013.01); *H04R 2460/11* (2013.01)

(58) Field of Classification Search
CPC .. H04R 1/1016; H04R 1/105; H04R 2201/10; H04R 1/10
See application file for complete search history.

(56) References Cited

U.S. PATENT DOCUMENTS

| 588,099 A | 8/1897 | Blount et al. |
| 931,768 A | 8/1909 | Kirkpatrick |
| 1,564,474 A | 12/1925 | Fensky |

(Continued)

FOREIGN PATENT DOCUMENTS

| CN | 1767694 A | 5/2006 |
| CN | 101437184 A | 5/2009 |

(Continued)

OTHER PUBLICATIONS

European Communication of Notices of Opposition (R. 79(1) EPC) and Communication of Further Notices of Opposition pursuant to Rule 79(2) EPC, dated Jul. 25, 2018, submitting the Communication of a Notice of Opposition, dated Jul. 18, 2018, for European Application No. 12178314.6.

(Continued)

*Primary Examiner* — Curtis A Kuntz
*Assistant Examiner* — Ryan Robinson
(74) *Attorney, Agent, or Firm* — Birch, Stewart, Kolasch & Birch, LLP

(57) ABSTRACT

A sub-tragus ear unit for comfortable wear of an in-ear ear unit is provided. The sub-tragus ear unit achieves the technical effect by separating the earphone from the attachment functionality that is provided by a separate anchor, wherein the earphone is attached to said anchor.

31 Claims, 9 Drawing Sheets

(56) References Cited

U.S. PATENT DOCUMENTS

| | | |
|---|---|---|
| 1,614,987 A | 1/1927 | Langenbeck et al. |
| 1,668,890 A | 5/1928 | Curran et al. |
| 1,688,910 A | 10/1928 | Winship |
| 1,753,817 A | 4/1930 | Aber |
| 1,893,143 A | 1/1933 | Koch |
| 1,969,559 A | 8/1934 | Kelly |
| 2,353,070 A * | 7/1944 | Pitkin, Jr. ............ H04R 1/1008 379/430 |
| 2,437,490 A | 3/1948 | Watson et al. |
| 2,521,414 A | 9/1950 | Schier |
| 2,545,731 A | 3/1951 | French |
| 2,595,489 A | 5/1952 | Rutter et al. |
| 2,763,334 A | 9/1956 | Starkey |
| 2,908,343 A | 10/1959 | Hummert |
| 2,910,980 A | 11/1959 | Stewart |
| 3,000,462 A | 9/1961 | Smith |
| 3,053,061 A | 9/1962 | French |
| 3,157,245 A | 11/1964 | Bernstein |
| D221,442 S | 8/1971 | Feingold |
| 4,010,820 A | 3/1977 | Johnson |
| 4,055,233 A | 10/1977 | Huntress |
| 4,219,018 A | 8/1980 | Draper, Jr. |
| D266,590 S | 10/1982 | Bennett |
| 4,353,364 A | 10/1982 | Woods |
| 4,429,194 A * | 1/1984 | Kamon ................ H04R 1/1016 381/371 |
| D274,814 S | 7/1984 | Tang |
| 4,540,063 A | 9/1985 | Ochi et al. |
| 4,646,872 A | 3/1987 | Kamon et al. |
| 4,864,610 A * | 9/1989 | Stevens .................. H04M 1/05 379/431 |
| 4,896,679 A | 1/1990 | St. Pierre |
| 4,965,838 A | 10/1990 | Kamon et al. |
| 4,972,492 A | 11/1990 | Tanaka et al. |
| D316,550 S | 4/1991 | Sogabe |
| D318,670 S | 7/1991 | Taniguchi |
| 5,048,090 A | 9/1991 | Geers |
| 5,055,233 A | 10/1991 | Borland et al. |
| D326,655 S | 6/1992 | Iribe |
| 5,222,151 A | 6/1993 | Nagayoshi et al. |
| 5,247,946 A | 9/1993 | Holder |
| 5,298,692 A | 3/1994 | Ikeda et al. |
| 5,305,387 A | 4/1994 | Sapiejewski |
| 5,548,643 A | 8/1996 | Dalgleish et al. |
| 5,625,171 A | 4/1997 | Marshall |
| 5,654,530 A | 8/1997 | Sauer et al. |
| 5,668,354 A | 9/1997 | Falco |
| D388,093 S | 12/1997 | Frengley |
| 5,712,453 A * | 1/1998 | Bungardt ............... H04R 1/105 181/135 |
| 5,727,566 A | 3/1998 | Leight |
| 5,957,136 A | 9/1999 | Magidson et al. |
| D430,139 S | 8/2000 | Peters et al. |
| D430,547 S | 9/2000 | Yoon |
| D430,860 S | 9/2000 | Yoon |
| 6,129,175 A | 10/2000 | Tutor et al. |
| 6,176,576 B1 | 1/2001 | Green et al. |
| 6,241,041 B1 | 6/2001 | Leight |
| 6,449,374 B1 | 9/2002 | Skulley et al. |
| D469,755 S | 2/2003 | Hlas et al. |
| D470,122 S | 2/2003 | Hlas et al. |
| D470,123 S | 2/2003 | Hlas et al. |
| D470,128 S | 2/2003 | Hlas et al. |
| D470,129 S | 2/2003 | Hlas et al. |
| D471,537 S | 3/2003 | Ham |
| D471,890 S | 3/2003 | Clarkson |
| D473,204 S | 4/2003 | Tanio |
| D478,991 S | 8/2003 | Dyer et al. |
| 6,637,910 B1 | 10/2003 | Mehler et al. |
| 6,683,965 B1 | 1/2004 | Sapiejewski |
| 6,688,421 B2 | 2/2004 | Dyer et al. |
| 6,690,807 B1 | 2/2004 | Meyer |
| 6,795,718 B2 | 9/2004 | Bae |
| 6,819,762 B2 | 11/2004 | Jones et al. |
| 6,820,717 B2 | 11/2004 | Fleming et al. |
| 6,868,284 B2 | 3/2005 | Bae |
| 6,879,697 B2 | 4/2005 | Topholm |
| D505,132 S | 5/2005 | Linville et al. |
| 6,944,307 B2 | 9/2005 | Berg |
| D510,574 S | 10/2005 | Okada |
| 6,961,440 B1 | 11/2005 | Schlaegel |
| 7,050,599 B2 | 5/2006 | Baskerville |
| 7,068,803 B2 | 6/2006 | Kuhlmann et al. |
| D525,962 S | 8/2006 | Elson |
| D538,271 S | 3/2007 | Kim et al. |
| 7,233,676 B2 | 6/2007 | Bayer |
| D558,735 S | 1/2008 | Carr et al. |
| 7,340,075 B2 | 3/2008 | Bayer |
| D566,099 S | 4/2008 | Komiyama |
| D566,691 S | 4/2008 | Andre et al. |
| D568,302 S | 5/2008 | Oh |
| D569,841 S | 5/2008 | Chung et al. |
| 7,394,910 B2 * | 7/2008 | Smith .................. H04R 1/1016 381/322 |
| D575,277 S | 8/2008 | Gaarde et al. |
| D575,772 S | 8/2008 | Schultz et al. |
| 7,412,068 B2 | 8/2008 | Bayer |
| D578,507 S | 10/2008 | Ando |
| D578,508 S | 10/2008 | Wang |
| D579,006 S | 10/2008 | Kim et al. |
| D582,389 S | 12/2008 | Bose et al. |
| D582,397 S | 12/2008 | Christopher |
| D582,398 S | 12/2008 | Nam et al. |
| D582,889 S | 12/2008 | Bose et al. |
| D584,284 S | 1/2009 | Carr et al. |
| D584,294 S | 1/2009 | Nam et al. |
| D585,881 S | 2/2009 | Nam et al. |
| D588,099 S | 3/2009 | Yuyama |
| D589,945 S | 4/2009 | Esses |
| 7,536,008 B2 * | 5/2009 | Howes .................. H04R 1/083 379/433.01 |
| 7,539,533 B2 | 5/2009 | Tran |
| D596,164 S | 7/2009 | Henning |
| D601,134 S | 9/2009 | Elabidi et al. |
| D602,476 S | 10/2009 | Lee et al. |
| D605,170 S | 12/2009 | Keinänen |
| D605,628 S | 12/2009 | Ando |
| D607,875 S | 1/2010 | Pedersen, II |
| D618,219 S | 6/2010 | Burgett et al. |
| D618,221 S | 6/2010 | Fahrendorff et al. |
| D620,927 S | 8/2010 | Li |
| D621,817 S | 8/2010 | Brickstad |
| D622,265 S | 8/2010 | Rye |
| D622,704 S | 8/2010 | Fahrendorff et al. |
| 7,778,410 B2 | 8/2010 | Liu et al. |
| 7,778,435 B2 | 8/2010 | Smith et al. |
| D628,188 S | 11/2010 | Koch |
| D633,481 S | 3/2011 | Chen |
| D634,305 S | 3/2011 | Hoggarth |
| 7,949,127 B2 | 5/2011 | Pedersen et al. |
| D640,670 S | 6/2011 | Rye |
| 7,965,855 B1 | 6/2011 | Ham |
| D641,747 S | 7/2011 | Gisborne |
| 8,009,853 B2 | 8/2011 | Ito et al. |
| D645,458 S | 9/2011 | Silvestri et al. |
| 8,139,806 B2 | 3/2012 | Hosaka et al. |
| 8,374,375 B2 * | 2/2013 | Hu ....................... H04R 1/1016 381/328 |
| 8,465,151 B2 | 6/2013 | Howell et al. |
| 8,532,324 B2 * | 9/2013 | Oosato ................ H04R 1/1008 381/370 |
| 8,538,056 B2 | 9/2013 | Ishibashi et al. |
| 8,540,363 B2 | 9/2013 | Abreu |
| 8,611,969 B2 | 12/2013 | Smith et al. |
| 8,630,436 B2 | 1/2014 | Berg |
| 8,696,113 B2 | 4/2014 | Lewis |
| 8,873,786 B2 | 10/2014 | Larsen et al. |
| 8,897,480 B2 | 11/2014 | Tan et al. |
| 8,976,994 B2 * | 3/2015 | Howes .................. H04R 1/1016 381/380 |
| 8,976,995 B2 | 3/2015 | Berg |
| 9,118,990 B2 | 8/2015 | Hankey et al. |
| 9,146,397 B2 | 9/2015 | Jacobs et al. |
| 9,161,118 B2 * | 10/2015 | Howes .................. H04R 1/1016 |

(56) References Cited

U.S. PATENT DOCUMENTS

| | | | |
|---|---|---|---|
| 10,003,878 B2* | 6/2018 | Ushakov | H04R 1/1016 |
| 10,025,103 B2 | 7/2018 | Sugihara et al. | |
| 2002/0096391 A1 | 7/2002 | Smith et al. | |
| 2002/0131585 A1 | 9/2002 | Jones et al. | |
| 2002/0172386 A1 | 11/2002 | Bayer | |
| 2003/0059075 A1 | 3/2003 | Niederdrank | |
| 2003/0091210 A1 | 5/2003 | Baskerville | |
| 2003/0174853 A1 | 9/2003 | Howes et al. | |
| 2003/0199850 A1 | 10/2003 | Chavez et al. | |
| 2004/0045558 A1 | 3/2004 | Taylor et al. | |
| 2004/0163653 A1 | 8/2004 | Fleming | |
| 2004/0165743 A1 | 8/2004 | Bayer | |
| 2005/0008180 A1 | 1/2005 | Smith et al. | |
| 2006/0067556 A1 | 3/2006 | Bailey et al. | |
| 2006/0093178 A1 | 5/2006 | Chen | |
| 2006/0120546 A1* | 6/2006 | Tanaka | H04M 1/05 381/315 |
| 2006/0177080 A1 | 8/2006 | Smith | |
| 2006/0188122 A1 | 8/2006 | Smith | |
| 2006/0215864 A1 | 9/2006 | Espersen et al. | |
| 2007/0116309 A1 | 5/2007 | Smith | |
| 2007/0183615 A1 | 8/2007 | Wurfel | |
| 2007/0254725 A1 | 11/2007 | Smith | |
| 2008/0085030 A1 | 4/2008 | Smith | |
| 2008/0159577 A1 | 7/2008 | Smith | |
| 2008/0181441 A1 | 7/2008 | Smith | |
| 2008/0247561 A1 | 10/2008 | Smith | |
| 2008/0298626 A1* | 12/2008 | Dean | H04R 1/105 381/381 |
| 2009/0092269 A1 | 4/2009 | Nielsen et al. | |
| 2009/0141923 A1 | 6/2009 | Smith | |
| 2009/0180654 A1 | 7/2009 | Nielsen | |
| 2009/0202094 A1 | 8/2009 | Ammitzboll et al. | |
| 2009/0202098 A1 | 8/2009 | Chan et al. | |
| 2009/0226025 A1 | 9/2009 | Howes et al. | |
| 2009/0285436 A1 | 11/2009 | Lowry | |
| 2009/0296975 A1 | 12/2009 | Uchida et al. | |
| 2009/0323993 A1 | 12/2009 | Slemming et al. | |
| 2010/0217098 A1 | 8/2010 | LeBoeuf et al. | |
| 2010/0278364 A1 | 11/2010 | Berg | |
| 2011/0280425 A1 | 11/2011 | Gibbons | |
| 2012/0039500 A1 | 2/2012 | Silvestri et al. | |
| 2012/0039501 A1 | 2/2012 | Silvestri et al. | |
| 2012/0128192 A1 | 5/2012 | Burgett et al. | |
| 2012/0321114 A1 | 12/2012 | Ishibashi et al. | |
| 2013/0235328 A1 | 9/2013 | Cauvet et al. | |
| 2014/0140567 A1 | 5/2014 | LeBoeuf et al. | |
| 2015/0071477 A1* | 3/2015 | Mainini | H04R 1/105 381/380 |

FOREIGN PATENT DOCUMENTS

| | | |
|---|---|---|
| CN | 201608862 U | 10/2010 |
| CN | 102378077 A | 3/2012 |
| CN | 102611957 A | 7/2012 |
| CN | 102742296 A | 10/2012 |
| DE | 89 11 607.0 U1 | 3/1990 |
| DE | 29718483 U1 | 2/1999 |
| DE | 101 17 705 A1 | 10/2001 |
| DE | 10141800 C1 | 1/2003 |
| DE | 202011002165 U1 | 5/2011 |
| EP | 0368125 A2 | 5/1990 |
| EP | 0786241 B1 | 7/2003 |
| EP | 1377113 A2 | 1/2004 |
| EP | 1594340 A1 | 11/2005 |
| EP | 2645736 A1 | 10/2013 |
| EP | 2690883 B1 | 10/2017 |
| FR | 2 437 802 | 4/1980 |
| FR | 2636144 A1 | 3/1990 |
| GB | 832311 A | 4/1960 |
| GB | 833506 | 4/1960 |
| GB | 2396421 A | 6/2004 |
| JP | 55-104889 U | 7/1980 |
| JP | 2001-333484 A | 11/2001 |
| JP | 2002-58086 A | 2/2002 |
| JP | 2005-184579 A | 7/2005 |
| JP | 2011-61725 A | 3/2011 |
| JP | 2012-124587 A | 6/2012 |
| KR | 10-2006-0084375 A | 7/2006 |
| WO | WO 01/50813 A2 | 7/2001 |
| WO | WO 01/50993 A1 | 7/2001 |
| WO | WO 02/45390 A1 | 6/2002 |
| WO | WO 03/096745 A1 | 11/2003 |
| WO | WO 2004/068896 A2 | 8/2004 |
| WO | WO 2004/100508 A1 | 11/2004 |
| WO | WO 2006/104981 A2 | 10/2006 |
| WO | WO 2007/014950 A2 | 2/2007 |
| WO | WO 2008/012401 A1 | 1/2008 |
| WO | WO 2008/147215 A1 | 12/2008 |
| WO | WO 2009/018825 A1 | 2/2009 |
| WO | WO 2009/030229 A1 | 3/2009 |
| WO | WO 2009/143055 A1 | 11/2009 |
| WO | WO 2010/031775 A1 | 3/2010 |
| WO | WO 2010/040350 A1 | 4/2010 |
| WO | WO 2010/040351 A1 | 4/2010 |
| WO | WO 2010/131426 A1 | 11/2010 |
| WO | WO 2011/006681 A1 | 1/2011 |
| WO | WO 2013/016336 A2 | 1/2013 |
| WO | WO 2013/158478 A1 | 10/2013 |
| WO | WO 2014-017922 A1 | 1/2014 |

OTHER PUBLICATIONS

Poldy, "Headphones," Chapter 14 of Loudspeaker & Headphone Handbook, Edited by John Borwick, 3rd Edition, 2001, pp. 585-692 (123 pages total).

International Preliminary Report on Patentability (Forms PCT/IPEA/416 and PCT/IPEA/409) for International Application No. PCT/NO2016/050055, dated Jul. 25, 2017.

International Search Report (Form PCT/ISA/210) for International Application No. PCT/NO2016/050055, dated Oct. 17, 2016.

Written Opinion of the International Searching Authority (Form PCT/ISA/237) for International Application No. PCT/NO2016/050055, dated Oct. 17, 2016.

English translation of Korean Office Action, dated Dec. 20, 2018, for Korean Application No. 10-2015-7002294.

English translation of Chinese Office Action and Search Report, dated May 29, 2019, for Chinese Application No. 201810757053.6.

Korean Office Action, dated May 17, 2019, for Korean Application No. 10-2019-7005112, with English translation.

* cited by examiner

A-A

A-A

A-A

A-A

Fig. 7
A-A
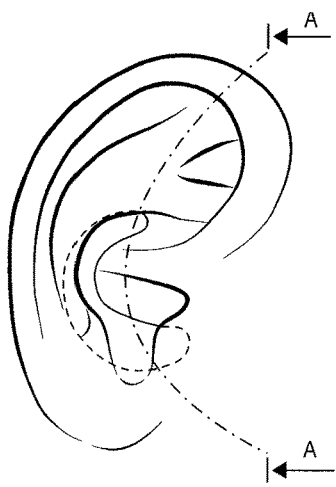
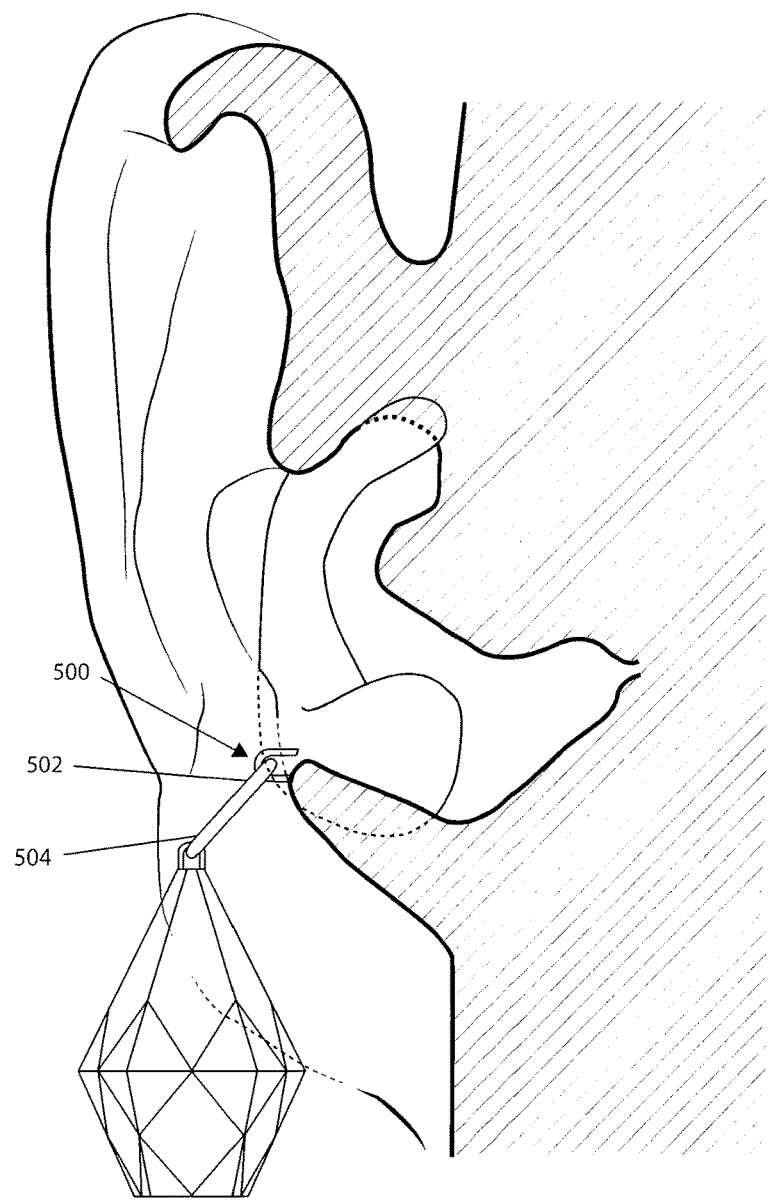

SUB TRAGIC EAR UNIT

BACKGROUND OF THE INVENTION

Technical Field

The invention relates to a system for removable ear attachment in general and in particular a sub-tragus ear unit for comfortable attachment of an ear unit.

Background Art

Microphone/earpiece combinations, wireless or attached by wire, to telephones, music systems, switchboards etc. are well known. A wide variety of solutions exist.

One solution is known as the "in-ear" solution, wherein the sound emitting device, also known as a hearing element, enters the ear canal. Typically a housing unit comprising a hearing element is positioned inside the concha and within the tragus and anti tragus, while a funnel ducts the sound into the ear canal. Frequently the funnel is provided with a gasket having flanges to dampen ambient sounds.

Typically such devices use the ear canal for attachment. While the solution is compact, removes ambient sound efficiently and also allows for good audio fidelity it suffers from the disadvantage of being uncomfortable due to pressure exerted on the pressure sensitive ear canal.

Another solution is the "on ear" solution, wherein the hearing element is held against the ear having a concha. This geometry allows for a wide hearing element to be placed flat against the concha. Unlike the in ear solution, this solution requires a separate means for holding the hearing element in position over the concha and several such means are well known in the art, such as over-head attachment, headband and over-ear attachment. This solution is simple but suffers from long term discomfort due to pressure exerted on the ear by the means for holding. There can also be problems with ambient sound entering the ear unless a sound absorbing cushion is used that encloses the ears fully bringing in other disadvantages such as large size.

A third solution is the "ear bud" solution where a housing unit comprising a hearing element is positioned inside the concha and held in place by tragus and anti tragus. In this way the housing unit also forms the means for holding the hearing element in place. While compact the disadvantage is discomfort due to pressure exerted on the tragus and anti tragus and also that it is difficult to exclude ambient sounds. If the pressure against the tragus and anti tragus is reduced the ear bud then is rather loose and can easily fall out.

A fourth solution is proposed by the present applicant as disclosed in WO/2002/045390 relating to an earpiece having a C-shape, and WO/2008/147215 relating to an improved earpiece having a curve and a curvature. Both disclose comfortable means for stable attachment to an anti helix of an ear. The former discloses an open solution that allows the auditory canal to remain open to the surroundings to a certain degree, which provides better comfort than a unit that blocks or closes off the auditory canal. This provides air circulation at the expense of admitting ambient sounds.

For the fifth solution one should refer to in-ear speakers as disclosed in WO/2009/143055 where a hearing element is placed into the concha and facing the tragus, perpendicular to that of the on-ear solution. The problem is stable positioning of the hearing element and discomfort relating to the edge of the hearing element is pressed against the inner wall of the concha when positioned in the ear.

References should also be made to the following documents:

GB833506, relating to a plug for an ear canal, wherein the plug enters the ear canal, U.S. Pat. No. 5,712,453, relating to a concha stabiliser, wherein a headset comprises a tubular extension or a voice tube extending down and towards a user's mouth, WO2004/068896, relating to an ambidextrous ear piece having a D-shape comprising an arcuate rib and a vertical rib, wherein the earpiece is provided with a boss that fits a wearer's ear canal, WO03/096745, relating to a crescent shaped hearing enhancement aid, wherein all figures clearly show the crescent shaped device is retracted well away from the tragus, U.S. Pat. No. 3,053,061, relating to inserts which are individually molded and sculptured to fit into ears of a user.

FR2437802, relating to ear attachment for earrings,

DE8911607 U1, relating to ear attachment, and

DE10117705, relating to a sound dampening device for use with ear units.

BRIEF DISCLOSURE OF THE INVENTION

Problems to be Solved by the Invention

Therefore, a main objective of the present invention is to provide a system for a compact and comfortable solution having an improved attachment that does not cause discomfort in the ear canal and is also capable of excluding ambient sound Means for Solving the Problems The objective is achieved according to the invention by an ear unit as defined in the preamble of claim 1, having the features of the characterising portion of claim 1.

The objective is also achieved according to the invention by a load bearing anchor as defined in the preamble of claim 5, having the features of the characterising portion of claim 5.

The present invention attains the above-described objective by separating the attachment, transducer and optionally occlusion functionalities into two distinct parts:

an anchor that provides stable attachment relative to an ear, and an hearing element connected to said anchor and that comprises the transducer which provides sound, wherein the hearing element is provided with an aperture which when the ear unit is positioned into an ear having a concha and a tragus, the aperture enters a sub-tragus region, thus projecting the sound into the sub-tragus region.

The aperture can be an opening by the hearing element.

The hearing element can be further be provided with an audio duct having an audio duct opening in which case the aperture is said audio duct opening.

Optionally the hearing element provides an occlusion.

Optionally the occlusion can be perforated with holes that are large enough to admit diffusion of air, yet small enough to prevent sound propagation.

The present invention attains the above-described objective by a load bearing anchor for stable fitting to an ear having an antihelix and a tragus, comprising a curve having an upper end and a lower end, wherein parts of the curve falls along the inner part of the antihelix, wherein the lower end extends into an extended lower end which is partly positioned under the tragus, preventing the distortion of the concha by keeping the antihelix at a substantially constant distance from the tragus when the anchor is positioned into the ear and a force is applied to the anchor in the direction of the intertragic notch.

Effects of the Invention

The technical differences over prior art is that a sub-tragus system is provided wherein the attachment is provided by an anchor and not by any elements protruding into the ear canal.

These effects provide in turn several further advantageous effects:
- it makes it possible to avoid bulky holding means as for the on-ear solutions and instead use light weight anchors such as those of the fourth solution,
- it avoids discomfort related to elements entering the ear canal,
- it allows for a light weight structure,
- it avoids discomfort relating to pressure exerted on the tragus and anti tragus, and
- it enables stable positioning in the ear without exerting uncomfortable pressure against the concha Optionally it also allows for further advantageous effects:
- it allows for excluding ambient sound without use of a large absorbing cushion around the ear, and
- it allows for air circulation.

The technical differences over prior art is that the anchor does not fill the entire concha but instead comprises two branches, the first branch falls along the inner part of the antihelix and the second branch extends into an extended lower end which is partly positioned under the tragus. Normally, when a force is applied to the concha in the downward direction when a person is standing up, the concha will deform slightly by elongating in the direction of the force and narrowing in a direction perpendicular to said force, thus the tragus and antitragus comes closer. However with the anchor according to this invention inserted the two branches will resist the narrowing. At the same time the force is distributed across a large area.

These effects provide in turn several further advantageous effects:
- it make sit possible to use lighter and more unobtrusive means for attachment,
- it provides more comfort in that there is less deformation of the ear
- the reduced deformation allows for larger load bearing without discomfort than means that permit deformation of the concha

BRIEF DESCRIPTION OF THE DRAWINGS

The invention will be further described below in connection with exemplary embodiments which are schematically shown in the drawings, wherein:

FIG. 7 shows an alternative use of a load bearing anchor wherein the attachment part extends from the curve through the intertragic notch.

DESCRIPTION OF THE REFERENCE SIGNS

The following reference numbers and signs refer to the drawings:

| | |
|---|---|
| 10 | Pinna |
| 11 | Helix |
| 12 | Crus of helix |
| 13 | Antihelix |
| 14 | Crura of antihelix |
| 15 | Superior crux |
| 16 | Inferior crux |
| 17 | Fossa triangularis |
| 18 | Sulcus auriculae posterior |
| 21 | Tragus |
| 22 | Antitragus |
| 23 | Incisura intertragica, intertragic notch |
| 24 | Concha |
| 25 | Cymba concha |
| 26 | Cavum concha |
| 27 | Scapha |
| 28 | Sub-tragus region |
| 29 | Tympanic membrane, eardrum |
| 30 | Ear canal |
| 100 | Ear unit |
| 200 | Anchor |
| 210 | Curve |
| 212 | Upper end |
| 214 | Lower end |
| 216 | Extended lower end |
| 218 | Curvature |
| 300 | Housing |
| 350 | Hearing element |
| 352 | Hearing element opening |
| 354 | Audio duct |
| 356 | Audio duct opening |
| 360 | Electroacoustic element |
| 370 | Gasket |
| 372 | Flanges |
| 400 | Part extending downwards |
| 500 | Attachment part |
| 502 | Attachment arm |
| 504 | Attachment end |
| 600 | Sound damping element |
| 610 | Shell |
| 620 | Connector to attachment part |

DETAILED DESCRIPTION

Anatomy of the Human Ear

Figure 1A:
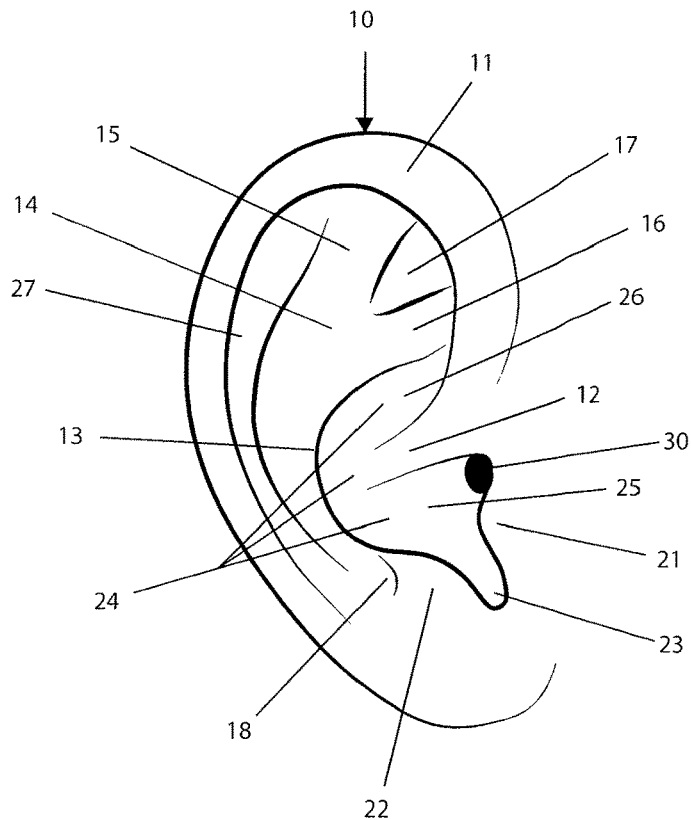
FIG. 1A shows the anatomy of a human ear from the outside.

In order to gain an understanding of the background of the invention it is important to know the anatomical details of the human ear, in particular of the outer ear, as shown in FIG. 1A. Outer ear 10, also known as pinna comprises a plurality of features of significance. Outermost is helix 11 tracing the periphery of the ear upwards and in towards the skull where it transitions into crus of helix 12. Within this is antihelix 13 which in the upward direction bifurcates into crura of antihelix 14, comprising superior crux 15 and inferior crux 16, separated by fossa triangularis 17. Below antihelix is sulcus auriculae posterior 18 and further below that again is antitragus 22 which is opposite tragus 21, separated by incisura intertragica 23, also known as the intertragic notch. Within these again is concha 24 which comprises cymbal concha 25 and cavum concha 26, separated by crus of helix 12.

Immediately within and partially covered by the tragus is the entrance to the ear canal 30. It is important to realize that this entrance is still a part of cavum concha. The ear canal proper extends from the deepest part of the concha to the eardrum 29, a distance of about 2.5 cm and approximately 4 cm from the tragus. The ear canal comprises an approximately 8 mm lateral cartilaginous part and an approximately 16 mm medial osseous part. It should also be noted that it is typically quite uncomfortable to have any foreign object in the ear canal. The ear canal is partially visible from the outside and is indicated in FIG. 1A.

Figure 1B:
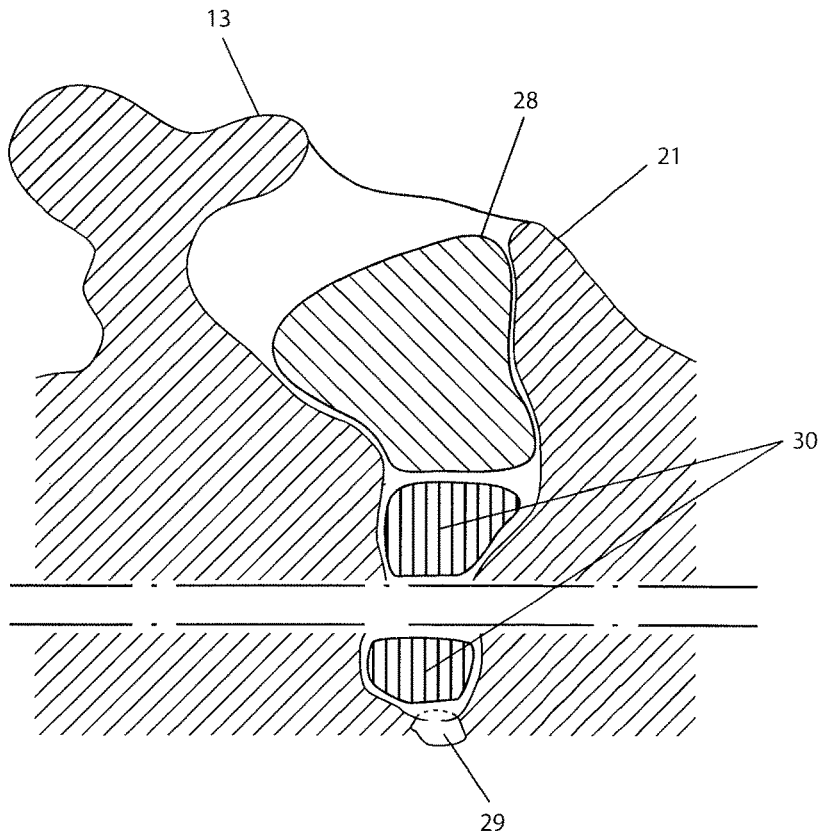
FIG. 1B shows a cross section the anatomy of a human ear along A-A.

This area immediately within and partially covered by the tragus 21 does not have an official anatomical name. Since this area is central to the invention and has acoustic and other distinguishing properties relating to comfortable wear it has been called the sub-tragus region 28 for the purpose of this document and is shown in FIG. 1B. The ear canal 30 is located below the sub-tragus region.

Principles Forming the Basis of the Invention

Figure 2A:
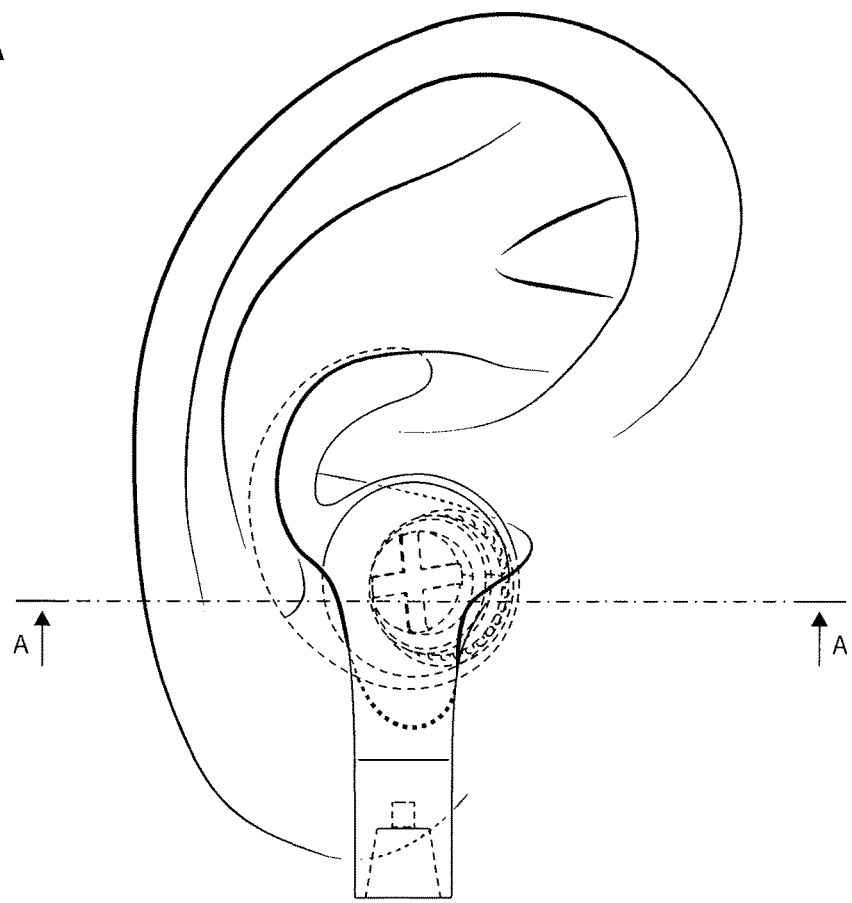
FIG. 2A shows the operating principles of the present invention, with an ear unit inserted into an ear as seen from the outside.

FIG. 2A shows the operating principles of the present invention, with an ear unit inserted into an ear as seen from the outside. A line A-A indicates a section for FIG. 2B and FIG. 2C. The anchor 200 comprises the curve 210 having an upper end 212, a lower end 214 and a curvature 218. Due to the angles it is not possible to clearly show all components of the anchor in all figures.

The underlying principle is that by separating the anchoring function 200 from the hearing element 350 it becomes possible to position the hearing element 350 in an optimal position without causing discomfort. By further positioning the hearing element so that it projects in underneath the tragus 21 and enters the sub-tragus area 28, sound is directed into the ear canal without the discomfort that is associated with having a foreign object entering the ear canal. The hearing element 350 is provided with a hearing element opening 352 where the opening or aperture faces the opening to the ear canal which extends from the sub-tragus area.

It should also be noted that the hearing element, enabled by the separate anchoring, projects underneath the tragus. This can be achieved in several ways.

Figure 2B:
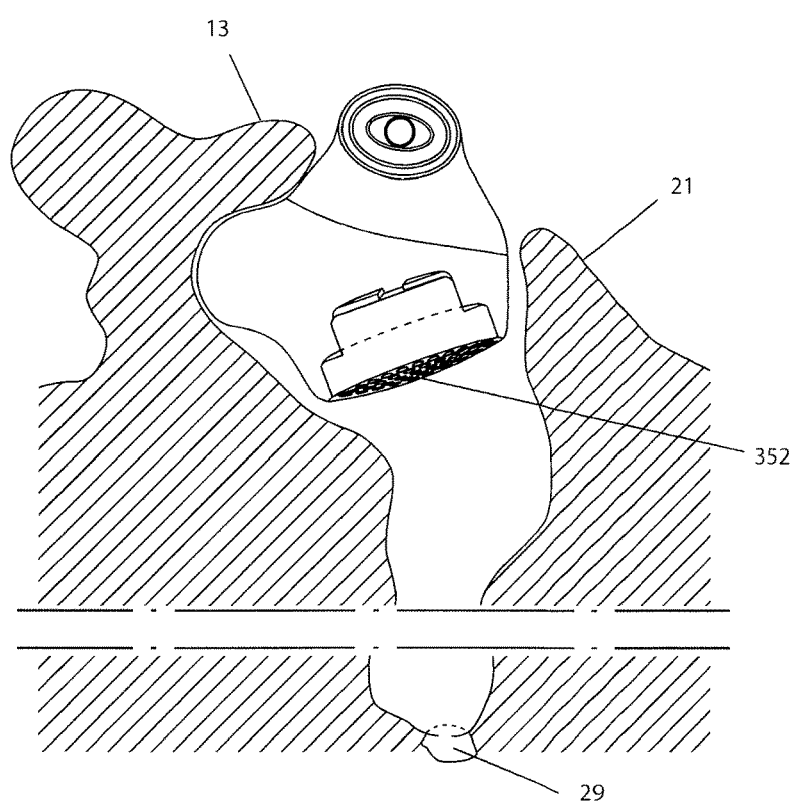
FIG. 2B shows the operating principles of the present invention in an intersection along A-A in a first embodiment.
Figure 2:
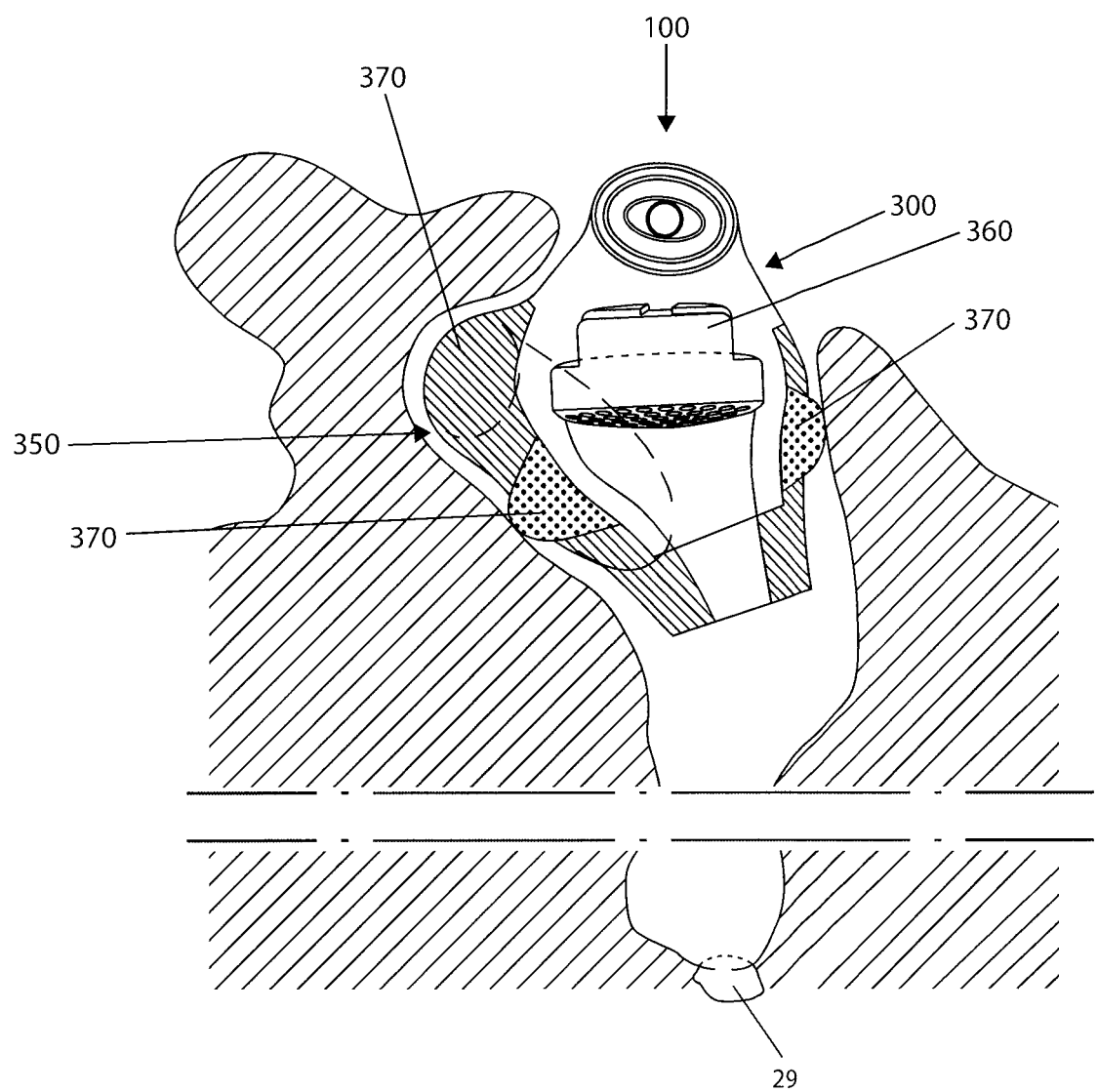
FIG. 2C shows the operating principles of the present invention in an intersection along A-A in a second embodiment.

In a first embodiment a hearing element 350 in the form of an electro acoustic transducer 360 is positioned underneath the tragus. Said hearing element is dimensioned to fit in the sub-tragus region. FIG. 2B shows schematically the above construction.

In a second embodiment the hearing element 350 comprises an electro acoustic transducer 360 attached to an audio duct 354 provided with an audio duct opening 356. As long as the audio duct is smaller than the wavelength of the sound, having a frequency of typically 20 Hz to 20000 Hz, corresponding to a wavelength of 15 m to 15 mm respectively, sound is conducted without significant distortion and the effective aperture becomes the opening of the audio duct.

This second embodiment allows for having the electro acoustic transducer larger than that of the first embodiment by retracting it away from the tragus. Since the effective hearing element is the end of the funnel and that this end projects into the sub-tragus region the technical effect is the same as for the first embodiment FIG. 2C shows schematically the above construction.

This second embodiment also allows for the electro acoustic transducer to be oriented at an angle that is not parallel to the plane of the audio duct opening. It is preferred that this audio duct opening is perpendicular to the entrance over the ear canal.

It should be noted that the on ear construction will involve structures that are of the order of the wavelength of high frequency sound, particularly relating to the size of the concha but potentially also of the hearing element according to the fifth solution.

In one embodiment the audio duct is not in contact with the concha or the tragus. The separation distance will be small compared to the wavelength of the sound and this will therefore lead to a damping of ambient sound, depending on separation distance, length of the audio duct and acoustic impedance mismatch.

Best Modes of Carrying Out the Invention

Figure 3:
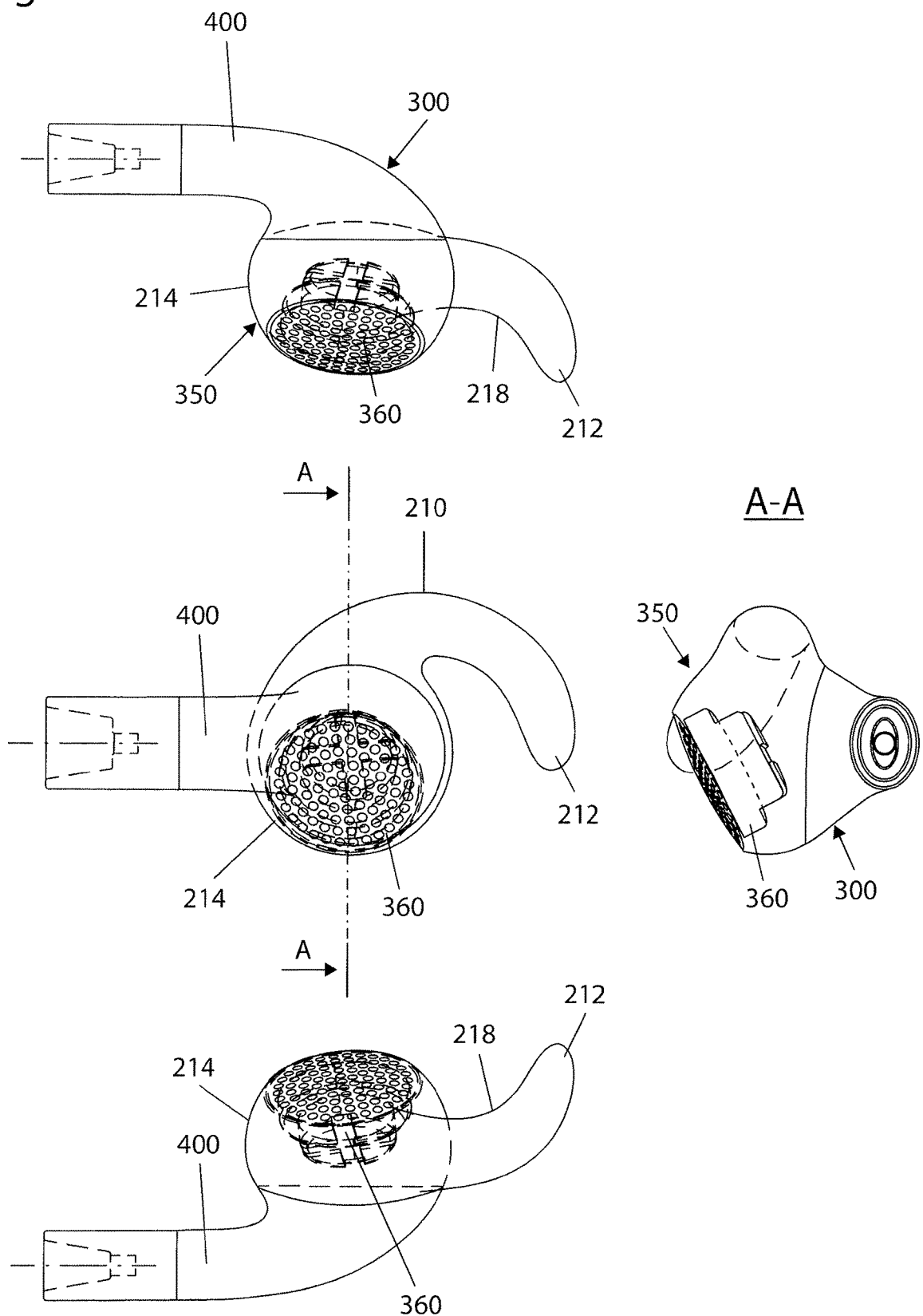
FIGS. 3 and 4 show two preferred embodiments of the present invention.
Figure 4:
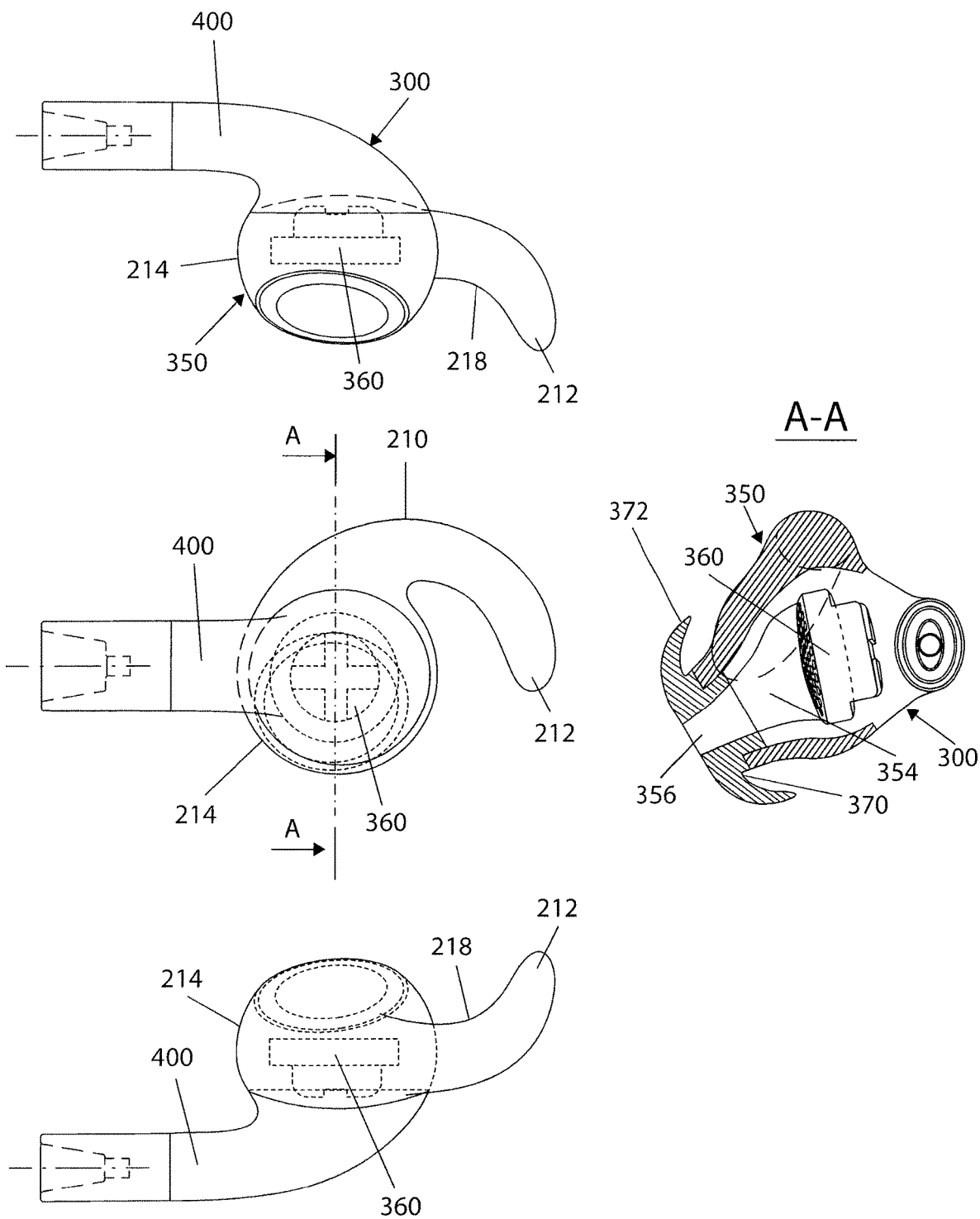

The embodiment of the ear unit according to the invention shown in FIGS. 3 and 4 comprises an anchor similar to the applicant's applications, specifically the C-shape as disclosed in WO12002/045390, and the improved earpiece having a curve 210 and a curvature 218 as disclosed in WO/2008/147215, the curve having an upper end 212 and a lower end 214. A hearing element 350 in the form of an electro acoustic transducer 360 formed as a part of a housing 300 which in turn is attached to said anchor so that when the ear unit is positioned into an ear having a concha and a tragus, the hearing element enters a sub-tragus region 28, where the concha 24 is covered by the tragus 21.

The hearing element 350 is further provided with a gasket 370 arranged substantially around a periphery of the hearing element in order to further stabilise the position of the hearing element as well as provide extra damping of ambient sound. The gasket is preferably made from a resilient material that easily shapes itself to the anatomical details of the ear without exerting uncomfortable pressure. Said gasket is further preferably detachable so that a user can remove it if it is preferred to hear some ambient sound or to change between different sizes and shapes to select the most comfortable size and shape. The gasket can comprise one or more flanges 372.

The housing 300 is the mechanical interface between the anchor 200 and the hearing element 350 and is typically suited for holding electronics, wire attachments and the like.

While the anchor is shown in prior art as having a clearly defined lower end, it is within the scope of the definition that the lower end can be embedded in a larger unit such as a housing part. FIG. 3 and FIG. 4 both show such a larger part surrounding the lower end. Due to the angles it is not possible to clearly show all components of the anchor in all figures.

Alternative Embodiments

Figure 6:
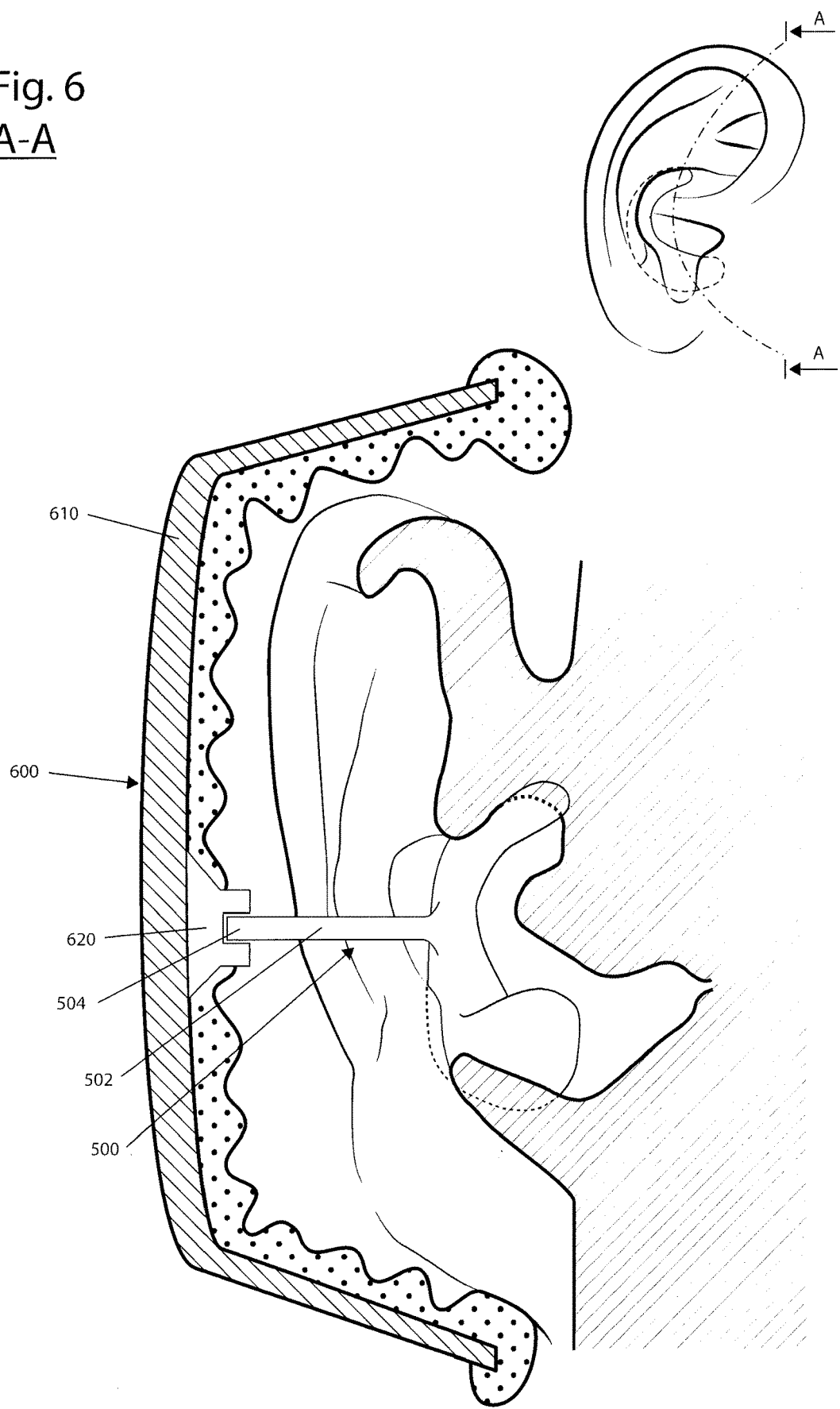
FIG. 6 shows a sound damping element attached to the load bearing anchor.

A number of variations on the above can be envisaged. For instance damping of ambient sound can be achieved by attaching a sound damping unit 600 to the anchor. Said sound damping unit is positioned so that when the ear unit is positioned into an ear the sound damping element is located over the concha. This is shown in FIG. 6.

The sound damping element typically comprises a shell 610 and a connector to attachment part 620. The attachment part is adapted for connection to attachment end 504.

This solution avoids external means for attachment such as over-head attachment, headband and over-ear attachment.

The sound damping unit can be further stabilised by a part extending into fossa triangularis 17 and/or a part extending under the fold at the top of helix 11.

Depending on the size and mass of the sound damping unit and expected physical activity of the user the anchor may be optimised for a larger load bearing capacity than disclosed in WO/2002/045390 and WO/2008/147215. Prior art disclose a comfortable anchor for light weight applications. Light weight in this context means a weight that is so small that the concha is insignificantly distorted when positioned into an ear. The inventor has found that a larger weight can be supported if the anchor is modified to compensate or prevent said distortion. The inventor found that a larger weight pulls the concha down in the direction of gravity. If the user is lying down the pressure is exerted on the anti helix and the curve will distribute the force over a sufficiently large area to avoid this being a problem. If the user is standing up right the force instead exerts in the direction of the intertragic notch. This would result in the concha being pulled downwards and also narrowed so that the area near the tragus would approach the area near the anti tragus.

Figure 5:
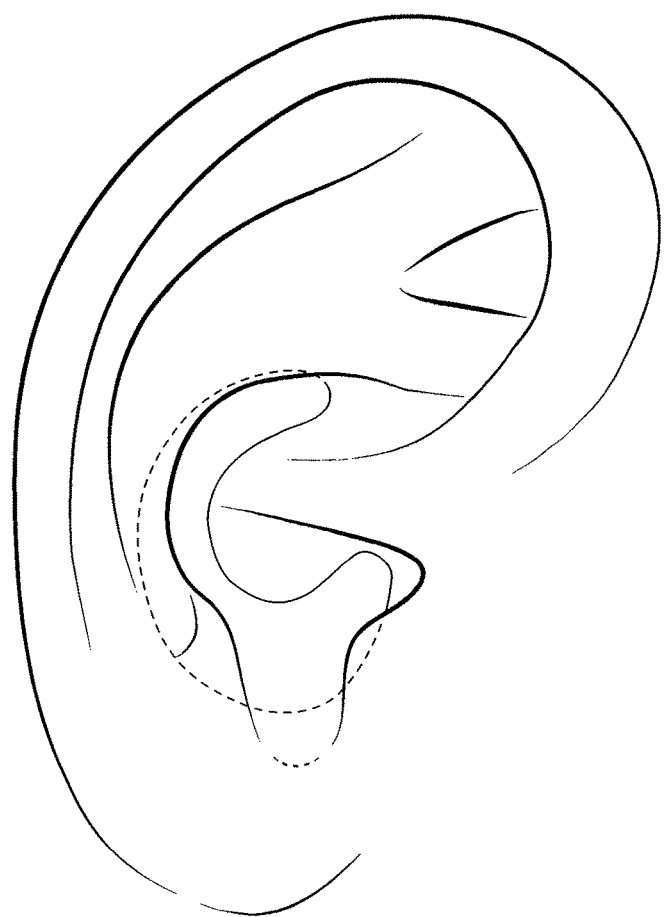
FIG. 5A shows an improved load bearing anchor inserted into an ear wherein the attachment part extends from the curve over the concha.
FIG. 5B shows the improved load bearing anchor of FIG. 5A close to the plane of the curve
FIG. 5C shows the improved load bearing anchor of FIG. 5C at a different angle.
Figure 5:
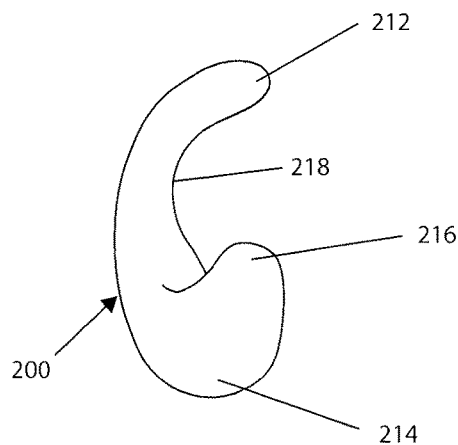
Figure 5:
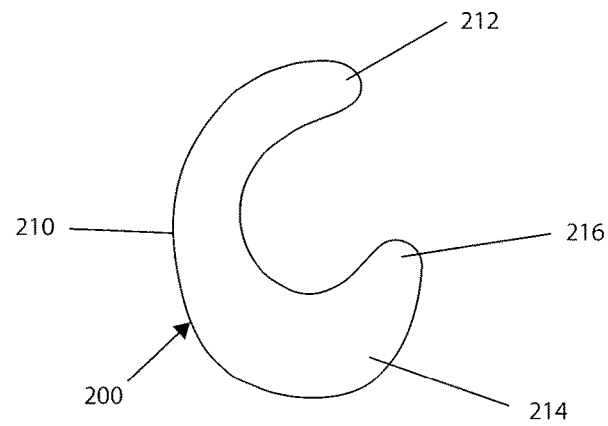

The inventor has found that by extending the lower end 214 of the anchor 200 further in the direction of the crus of helix 12 into an extended lower end 216 the problem of distortion is overcome by distributing the force over a wider area and also by countering the forces narrowing the concha. At the same time it is found that the upper end of the anchor does not have to project in underneath the flap covering the lower part of the cavity covered by the lower node of the antihelix of the ear. This is load bearing anchor is shown in FIG. 5B at an angle that highlights an optional curvature 218 in the curve 210, offering improved attachment. FIG. 5A shows the load bearing anchor having a part extending downwards inserted into an ear while FIG. 5C shows an anchor having no part extending downward.

The load bearing capacity can be further improved by having the upper end of the anchor engage the anterior part of the helix and/or the crus of helix.

Such a construction has a wide range of application in addition to holding a sound damping element. It could for instance be used to hold ear jewelry and avoid having to puncture the ear lobe for attachment purposes. Such jewelry can be so heavy that traditional ear attachment would be uncomfortable.

Attachments would typically be through an adaptor called attachment part 500 connected at a first end to the curve, the housing or both and adapted for attachment to external units. Typically the attachment part is provided with an attachment arm 502 to allow the attachment to be offset at a distance from the concha. At a second end of the attachment part, typically opposite the first end of the attachment part, an attachment end 504 is provided. Preferably this attachment end allows for guided attachment and/or detachment of external units while having the anchor still inserted in the ear.

In many cases the attachment part extends straight out from the area just outside the concha. Where further stability or load bearing capacity is required the attachment part extends through the intertragic notch, optionally contacting the intertragic notch.

A part extending out from the load bearing anchor would form a convenient and hygienic attachment. In a preferred embodiment the attachment part would extend from the anchor through the intertragic notch. This is shown in FIG. 7.

Optionally the ear unit can be provided with a part extending downward 400, providing room for battery, electronics, antennas or attachment facilities for wires. This also has the benefit of providing stability by lowering the centre of gravity. Preferably this part extending downwards passes through the intertragic notch and thus provides extra stability.

This part extending part downward can also provide a convenient basis for the attachment part.

The various solutions of prior have different properties in terms of occlusion and the ability to exclude or include ambient sounds.

| Type | Description | Occlusion |
|---|---|---|
| 1 | In-ear | Very good |
| 2a | On-ear without cushion | Open |
| 2b | On-ear with cushion | Quite good |
| 3 | Ear bud | Good |
| 4 | C-shape | Very open |
| 5 | Angled hearing element | Open |

It will be appreciated that occlusion in prior art is an inherent property of the design and is fixed with only very minor adjustments such as providing ear buds with extra gaskets will improve the degree of occlusion.

Figure 8:
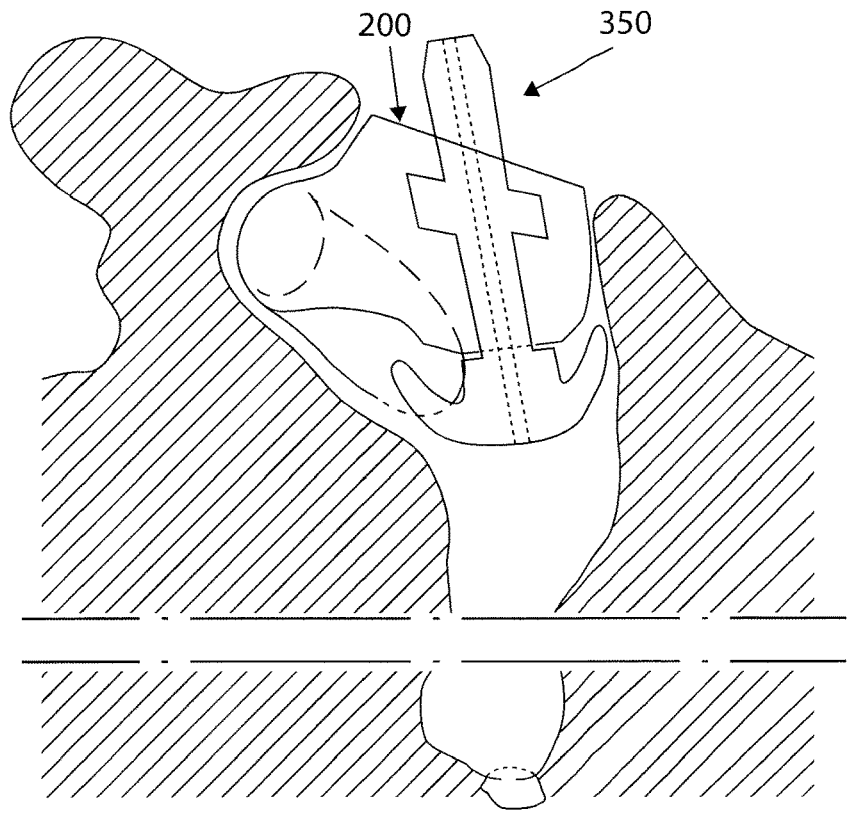
FIGS. 8A and 8B shows a hearing unit in an un-occluded position and in an occluded position respectively.
Figure 8:
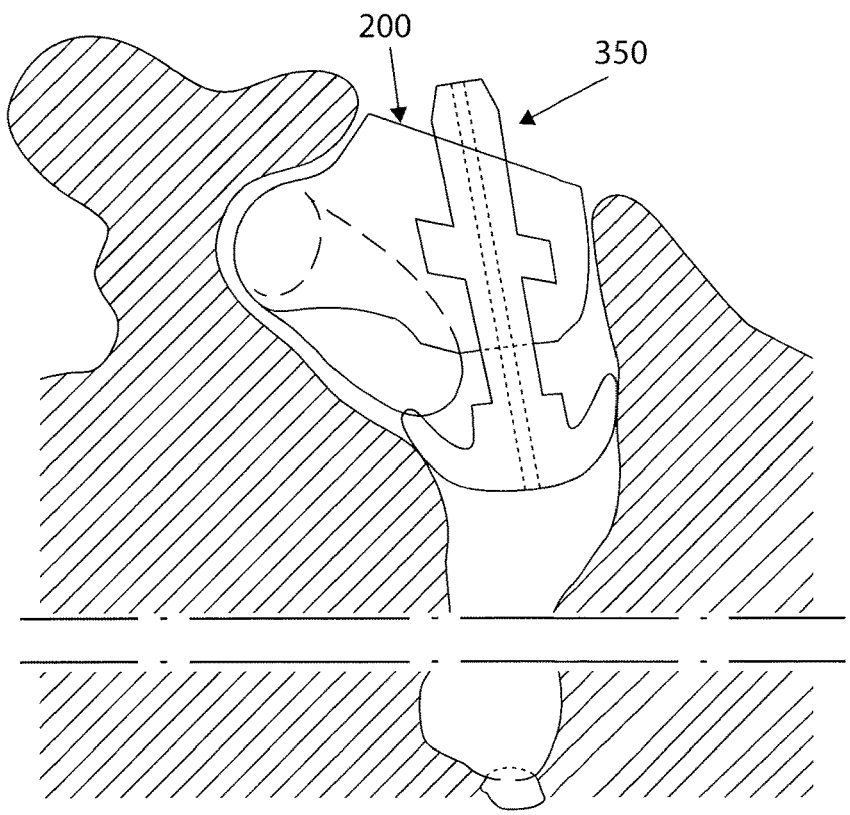

The inventors of the present invention has realised that by separating attachment functionality to an anchor separated from the hearing element it is possible to provide occlusion in a first inner position wherein the hearing element occludes the opening to the ear canal, and be retracted relative to the anchor into a second position where a passage opens between the hearing element and the concha. It should be noted that the retraction can be away from the tragus, away from the opposite side of the concha from the tragus or both. Retraction in this context means both a movement outwards as well as reducing the cross section of the hearing element, for instance by deflation of a cushioning element or retraction of a gasket, optionally comprising flanges. The effect of this is to open for a passage around the parts occluding in the first position. FIGS. 8A and 8B shows a hearing unit in an un-occluded position and in an occluded position respectively.

Adjusting between the first and the second position can be made without removing the ear unit from the ear. One can envisage automatic position changes, for instance electro-mechanically, by inputs such as warning sounds or switching functionality between listening to music and making a telephone call.

The anchor can take on many forms as long as it provides a stable anchoring in the ear without the need for ear canal attachment and still remain within the scope of the invention. Such alternative anchors can be based on prior art, such as over head attachment, headband and over-ear attachment.

INDUSTRIAL APPLICABILITY

The invention according to the application finds use in ear attached units for holding a hearing element, and outer elements such as a sound damping element.

The invention claimed is:
1. A sub-tragus ear unit, comprising:
an anchor, configured to provide stable attachment of the ear unit relative to an ear; and
a hearing element comprising a transducer configured to provide sound, and connected to said anchor,
wherein the hearing element is provided with an aperture, wherein when the ear unit is positioned into an ear having a concha, a tragus and an ear canal, the aperture is configured to enter a sub-tragus region, thus projecting the sound into the sub-tragus region, the sub-tragus region being part of the concha which is at least partially covered by the tragus, wherein said aperture faces the opening to the ear canal such that the sound is directed into the ear canal, wherein the aperture is located entirely within the sub-tragus region, further comprising a part extending downward in the direction of gravity when standing up, and wherein the part includes a first portion connecting to the hearing element, and a second portion extending downward from the first portion, and the hearing element has an outlet surface provided with a plurality of apertures, and wherein a plane containing a longitudinal central axis of the first portion and a longitudinal central axis of the second portion is not orthogonal to a plane containing the outlet surface.

2. The sub-tragus ear unit according to claim 1, wherein the hearing element is an electroacoustic element.

3. The sub-tragus ear unit according to claim 2, further comprising a gasket for blocking external sound.

4. The sub-tragus ear unit according to claim 1, wherein the hearing element is provided with an audio duct having an audio duct opening, wherein the aperture is said audio duct opening.

5. The sub-tragus ear unit according to claim 4, further comprising a gasket for blocking external sound.

6. The sub-tragus ear unit according to claim 1, further comprising a gasket for blocking external sound.

7. The sub-tragus ear unit according to claim 1, further comprising an external sound damping element, wherein said sound damping element is attached to at least one of the anchor and a housing of the ear unit.

8. The sub-tragus ear unit according to claim 1, wherein the hearing element has an outlet surface provided with a plurality of apertures, and the ear unit is configured in such a manner that when the ear unit is positioned into the ear, a central axis normal to the outlet surface of the hearing element extends to intersect the ear canal, and wherein all of the plurality of apertures are located entirely within the sub-tragus region.

9. The sub-tragus ear unit according to claim 1, wherein the hearing element has an outlet surface provided with a plurality of apertures, and wherein an axis normal to a plane substantially containing a surface of the anchor contacting the concha when the ear unit is positioned into the ear intersects a central axis normal to the outlet surface of the hearing element.

10. The sub-tragus ear unit according to claim 1, wherein the ear unit is configured to provide occlusion, where the hearing element occludes the opening of the ear canal in a first inner position, and the hearing element is configured to be retracted relative to the anchor into a second position where a passage opens between the hearing element and the concha.

11. The sub-tragus ear unit according to claim 1, wherein a housing is a mechanical interface between the anchor and the hearing element.

12. The sub-tragus ear unit according to claim 11, wherein the aperture is an opening by the hearing element, and the hearing element is an electroacoustic element.

13. The sub-tragus ear unit according to claim 11, further comprising a gasket for blocking external sound.

14. The sub-tragus ear unit according to claim 11, further comprising a part extending downward in the direction of gravity when standing up.

15. The sub-tragus ear unit according to claim 11, wherein the hearing element is provided with an audio duct having an audio duct opening, and wherein the aperture is said audio duct opening.

16. A sub-tragus ear unit, comprising:
an anchor, configured to provide stable attachment of the ear unit relative to an ear; and
a hearing element comprising a transducer configured to provide sound, and connected to said anchor,
wherein the hearing element is provided with an aperture,
wherein when the ear unit is positioned into an ear having a concha, a tragus and an ear canal, the aperture is configured to enter a sub-tragus region, thus projecting the sound into the sub-tragus region, the sub-tragus region being part of the concha which is at least partially covered by the tragus,
wherein said aperture faces the opening to the ear canal such that the sound is directed into the ear canal,
wherein the aperture is located entirely within the sub-tragus region, and
wherein the ear unit is configured to provide occlusion, where the hearing element occludes the opening of the ear canal in a first inner position, and the hearing element is configured to be retracted relative to the anchor into a second position where a passage opens between the hearing element and the concha.

17. The sub-tragus ear unit according to claim 16, wherein a housing is a mechanical interface between the anchor and the hearing element.

18. The sub-tragus ear unit according to claim 17, wherein the hearing element is provided with an audio duct having an audio duct opening, and wherein the aperture is said audio duct opening.

19. The sub-tragus ear unit according to claim 17, wherein the aperture is an opening by the hearing element, and the hearing element is an electroacoustic element.

20. The sub-tragus ear unit according to claim 17, further comprising a gasket for blocking external sound.

21. The sub-tragus ear unit according to claim 17, further comprising a part extending downward in the direction of gravity when standing up.

22. The sub-tragus ear unit according to claim 16, wherein the hearing element is an electroacoustic element.

23. The sub-tragus ear unit according to claim 22, further comprising a gasket for blocking external sound.

24. The sub-tragus ear unit according to claim 16, wherein the hearing element is provided with an audio duct having an audio duct opening, wherein the aperture is said audio duct opening.

25. The sub-tragus ear unit according to claim 24, further comprising a gasket for blocking external sound.

26. The sub-tragus ear unit according to claim 16, further comprising a gasket for blocking external sound.

27. The sub-tragus ear unit according to claim 16, further comprising an external sound damping element, wherein said sound damping element is attached to at least one of the anchor and a housing of the ear unit.

28. The sub-tragus ear unit according to claim 16, wherein the hearing element has an outlet surface provided with a plurality of apertures, and the ear unit is configured in such a manner that when the ear unit is positioned into the ear, a central axis normal to the outlet surface of the hearing element extends to intersect the ear canal, and wherein all of the plurality of apertures are located entirely within the sub-tragus region.

29. The sub-tragus ear unit according to claim 16, wherein the hearing element has an outlet surface provided with a plurality of apertures, and wherein an axis normal to a plane substantially containing a surface of the anchor contacting the concha when the ear unit is positioned into the ear intersects a central axis normal to the outlet surface of the hearing element.

30. The sub-tragus ear unit according to claim 16, further comprising a part extending downward in the direction of gravity when standing up.

31. The sub-tragus ear unit according to claim 30, wherein the part includes a first portion connecting to the hearing element, and a second portion extending downward from the first portion, and the hearing element has an outlet surface provided with a plurality of apertures, and wherein a plane containing a longitudinal central axis of the first portion and a longitudinal central axis of the second portion is not orthogonal to a plane containing the outlet surface.

* * * * *